(12) United States Patent  
Assmann (10) Patent No.: US 10,687,940 B2  
(45) Date of Patent: Jun. 23, 2020

(54) ARRANGEMENT FOR MONITORING A POSITIONING OF A PROSTHETIC CARDIAC VALVE AND CORRESPONDING METHOD

(71) Applicant: Siemens Healthcare GmbH, Erlangen (DE)

(72) Inventor: Stefan Assmann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 431 days.

(21) Appl. No.: 15/603,594

(22) Filed: May 24, 2017

(65) Prior Publication Data

US 2017/0340442 A1 Nov. 30, 2017

(30) Foreign Application Priority Data

May 31, 2016 (DE) ........................ 10 2016 209 389

(51) Int. Cl.
*A61F 2/24* (2006.01)
*G16H 40/63* (2018.01)
(Continued)

(52) U.S. Cl.
CPC .......... *A61F 2/2427* (2013.01); *A61B 8/0841* (2013.01); *A61B 8/0883* (2013.01);
(Continued)

(58) Field of Classification Search
CPC ..... A61F 2/2427; A61B 34/20; A61B 8/0841; A61B 8/0883; A61B 8/12; A61B 8/42;
(Continued)

(56) References Cited

U.S. PATENT DOCUMENTS

2007/0276243 A1 11/2007 Gerard et al.
2009/0234444 A1* 9/2009 Maschke ................ A61B 5/411
623/2.11
(Continued)

FOREIGN PATENT DOCUMENTS

CN 1897878 A 1/2007
CN 104053404 A 9/2014
(Continued)

OTHER PUBLICATIONS

Chinese Office Action and English translation thereof dated Nov. 19, 2018.
(Continued)

*Primary Examiner* — Erich G Herbermann
(74) *Attorney, Agent, or Firm* — Harness, Dickey & Pierce, P.L.C.

(57) ABSTRACT

A prosthetic cardiac valve implantation arrangement is described. The prosthetic cardiac valve implantation arrangement includes a prosthesis catheter with a prosthetic cardiac valve to be implanted; and an ICE catheter for introduction into area surrounding a cardiac valve to detect a relative position and/or relative direction of orientation of the cardiac valve with respect to the ICE catheter with the aid of an ultrasound image of the cardiac valve recorded by the ICE catheter. In addition, a navigation system is for determining an absolute position and an absolute direction of orientation of the ICE catheter; and a control facility is for controlling the insertion of the prosthetic cardiac valve into the annulus of the cardiac valve on the basis of the ultrasound image recordings of the ICE catheter and positional and/or orientation-direction information from the navigation system. Also described is a method for monitoring a catheter-based prosthetic cardiac valve implantation.

10 Claims, 4 Drawing Sheets

(51) Int. Cl.
*A61B 8/08* (2006.01)
*A61B 8/00* (2006.01)
*A61B 34/20* (2016.01)
*A61B 8/12* (2006.01)
*A61B 90/00* (2016.01)

(52) U.S. Cl.
CPC .............. *A61B 8/12* (2013.01); *A61B 8/42* (2013.01); *A61B 8/4245* (2013.01); *A61B 34/20* (2016.02); *G16H 40/63* (2018.01); *A61B 2034/2051* (2016.02); *A61B 2034/2063* (2016.02); *A61B 2034/2072* (2016.02); *A61B 2090/364* (2016.02); *A61B 2090/3784* (2016.02)

(58) Field of Classification Search
CPC .......... A61B 8/4245; A61B 2034/2051; A61B 2034/2063; A61B 2034/2072; A61B 2090/1364; A61B 2090/3784; G16H 40/63
See application file for complete search history.

(56) References Cited

U.S. PATENT DOCUMENTS

| | | |
|---|---|---|
| 2011/0237940 A1 | 9/2011 | Raleigh |
| 2012/0259209 A1* | 10/2012 | Harhen ................ A61B 8/0841 |
| | | 600/424 |
| 2013/0150710 A1 | 6/2013 | Zentgraf et al. |
| 2015/0196368 A1 | 7/2015 | Ecabert et al. |

FOREIGN PATENT DOCUMENTS

| | | |
|---|---|---|
| CN | 104771227 A | 7/2015 |
| DE | 102009025250 B3 | 11/2010 |
| WO | WO 2014210299 A1 | 12/2014 |

OTHER PUBLICATIONS

German Office Action dated Feb. 1, 2017.
Chinese Office Action and English translation thereof dated May 24, 2019.

* cited by examiner

ARRANGEMENT FOR MONITORING A POSITIONING OF A PROSTHETIC CARDIAC VALVE AND CORRESPONDING METHOD

PRIORITY STATEMENT

The present application hereby claims priority under 35 U.S.C. § 119 to German patent application number DE 102016209389.4 filed May 31, 2016, the entire contents of which are hereby incorporated herein by reference.

FIELD

At least one embodiment of the invention generally relates to a prosthetic cardiac valve implantation arrangement. At least one embodiment of the invention further generally relates to a method for monitoring a catheter-based prosthetic cardiac valve implantation. At least one embodiment of the invention also generally relates to a use of a prosthetic cardiac valve implantation arrangement.

BACKGROUND

The human heart consists of a total of four chambers, the right atrium, the right ventricle, the left ventricle and the left atrium. Deoxygenated blood is pumped into the right atrium through the superior vena cava and the inferior vena cava and from there the deoxygenated blood passes through a first cardiac valve, the tricuspid valve, into the right ventricle. From the right ventricle, the deoxygenated blood passes through a second cardiac valve, the pulmonary valve, into the pulmonary artery. When the blood has absorbed oxygen in the lungs, it flows through the pulmonary veins to the left atrium of the heart. Then, the oxygenated blood passes through a third cardiac valve, the mitral valve, into the left ventricle. From there, the oxygenated blood passes through a fourth cardiac valve, the aortic valve, into the aorta from where it supplies all the human organs inter alia with oxygen.

As valves, the cardiac valves ensure that the blood only flows in one direction when pumped by the cardiac muscle. Stenotic or leaking cardiac valves present an acute hazard. In the first case, insufficient blood flows through the valve in question. In the second case, the valve function is impaired and too much blood flows back into the respective region before the cardiac valve structure, for example the left or right ventricle, even though the cardiac valve is closed. Problems with the cardiac valves are, for example, caused by calcareous deposits on the valves, by inflammation of the valves or cardiac muscle or can also be the result of myocardial infarction. Cardiac valve defects are also occasionally congenital.

As a rule, a several cardiac valve defect requires surgical treatment since otherwise there is a risk of permanent damage to the cardiac muscle resulting in gradually further reduced pump function, reduced physical capacity and ultimately greatly shortened life expectancy. Cardiac valve surgery is usually performed with an open thorax and arrested heart while a heart-lung machine maintains the circulation artificially. This always entails a certain risk of the patient suffering a stroke, which can be accompanied by impaired motor functions and impaired intellectual faculties.

Alternatively, for several years, it has also been possible to use a minimally invasive catheter-based method known by the acronym TAVI (TAVI=transcatheter aortic valve implantation). With TAVI, cardiac valves are implanted into the beating heart without open surgery. Therefore, there is no longer a need for connection to the heart-lung machine so that the described risk of stroke no longer exists. With a minimally invasive procedure of this kind, there is no need to remove the defective cardiac valve—it is merely pushed toward the side. A prosthesis, i.e. a biological cardiac valve, is now used instead of the old valve. This technique is generally used with particularly endangered patients in whom open surgery would be too risky. In this case, the prosthetic valve is introduced with the aid of a catheter, a thin flexible plastic wire, through the vessels as far as the heart and unfolded at the position of the defective cardiac valve. As a rule, access is either through the inguinal vessels or via the cardiac apex.

However, following the use of the TAVI method, it is not uncommon for paravalvular leaks to occur if the artificial cardiac valve was not inserted in an exactly planar manner into the existing aortic valve or the annulus, i.e. the base of the aortic valve. It is necessary to prevent the occurrence of such leaks since they could result in impairment of left-ventricular function and hemolysis.

To date, leaks of this kind have been sealed via an additional occluding element. However, this requires a further invention. Moreover, there is also a further implant in the region of the cardiac valve in addition to the prosthetic valve.

There are also so-called repositionable prosthetic valves but these are associated with risks with respect to stability in the annulus.

SUMMARY

At least one embodiment of the present invention discloses a device for the implantation of a prosthetic cardiac valve and a method for monitoring such a minimally invasive implantation of prosthetic cardiac valves with which the problems can be reduced or even avoided.

At least one embodiment of the present invention is directed to a prosthetic cardiac valve implantation arrangement method, a method for monitoring a catheter-based prosthetic cardiac valve implantation and a use of a prosthetic cardiac valve implantation arrangement.

At least one embodiment of the prosthetic cardiac valve implantation arrangement according to the invention comprises a prosthesis catheter with a prosthetic cardiac valve to be implanted. The prosthetic cardiac valve implantation arrangement also comprises an ICE catheter for introduction into the area surrounding a cardiac valve to be treated. An ICE catheter (ICE=intracardiac echocardiography) should be understood to be a catheter with an ultrasonic transceiver system at its tip, which is able to create ultrasound images within the heart. The ICE catheter is further used to detect a relative position and/or a relative direction of orientation of the cardiac valve with respect to the ICE catheter with the aid of an ultrasound recording of the cardiac valve by the ICE catheter and preferably for ultrasound recordings of the prosthesis catheter. In addition, one part of the prosthetic cardiac valve implantation arrangement is a navigation system for determining an absolute position and an absolute direction of orientation of the ICE catheter. Hereinafter, an absolute position or absolute direction of orientation should be understood to mean a corresponding position or direction of orientation in a fixed coordinate system. This coordinate system can, for example, be a coordinate system in which the external navigation system is based and which is used by the external navigation system. On the other hand, relative positional data or directions of orientation should be understood as meaning corresponding information in a coordinate system, which moves or rotates together with moving components, in this case, the ICE catheter.

With the method for monitoring a catheter-based prosthetic cardiac valve implantation according to an embodiment of the invention, control commands are output by a control facility for the introduction of an ICE catheter into an area surrounding a cardiac valve to be treated. The control commands can, for example, be displayed to an attending physician on a screen display or it can also be alternatively or additionally used to control an automated system for the introduction of the ICE catheter in the vicinity of the cardiac valve to be treated.

The use according to an embodiment of the invention is directed at a use of a prosthetic cardiac valve implantation arrangement according to the invention to carry out an implantation of a prosthetic cardiac valve. Advantageously, the use of the prosthetic cardiac valve implantation arrangement according to the invention reduces the risk of an imprecisely positioned prosthetic cardiac valve so that the patient does not have to undergo a corrective intervention or suffer the negative consequences of an imprecisely positioned cardiac valve.

Some of the components of the prosthetic cardiac valve implantation arrangement according to an embodiment of the invention can be embodied substantially in the form of software components. This applies in particular to parts of the navigation system and the control facility. However, in principle, in particular when particularly fast calculations are required, these can also be partially implemented in the form of software-supported hardware, for example FPGAs or the like. Similarly, for example if only a transfer of data from other software components is involved, the required interfaces can be embodied as software interfaces. However, they can also be embodied as hardware-based interfaces controlled by suitable software.

A substantially software-based implementation has the advantage that, after supplementing the hardware by a navigation system and a corresponding modification of an ICE catheter, control facilities for prosthetic cardiac valve implantation arrangements used to date can also be easily retrofitted by a software update in order to work in accordance with an embodiment of the invention. Insofar, a corresponding non-transitory computer program product is disclosed with a computer program, which can be loaded directly into a storage facility of a control facility of a prosthetic cardiac valve implantation arrangement, with program sections for carrying all the steps of the method according to an embodiment of the invention when the program is executed in the control facility. In addition to the computer program, a non-transitory computer program product of this can optionally comprise additional components such as, for example, documentation and/or additional components including hardware components, such as, for example, hardware keys (dongles etc.) for using the software.

To transport the control facility and/or for storage on or in the control facility, it is possible to use a non-transitory computer-readable medium, for example a memory stick, a hard disk or another transportable or permanently installed data carrier on which the program sections of the computer program that can be read and executed by a computing unit of the control facility are stored. To this end, the computing unit can, for example, comprise one or more interacting microprocessors or the like.

The claims and the following description each contain particularly advantageous embodiments and developments of the invention. Here, in particular the claims of one claims category can also be developed analogously to the dependent claims of a category. In addition, within the context of the invention, the various features of different example embodiments and claims can also be combined to form new example embodiments.

BRIEF DESCRIPTION OF THE DRAWINGS

The invention is described again in more detail with reference to the attached figures and to example embodiments. The figures show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a prosthetic cardiac valve implantation arrangement method, a method for monitoring a catheter-based prosthetic cardiac valve implantation and a use of a prosthetic cardiac valve implantation arrangement.

At least one embodiment of the prosthetic cardiac valve implantation arrangement according to the invention comprises a prosthesis catheter with a prosthetic cardiac valve to be implanted. The prosthetic cardiac valve implantation arrangement also comprises an ICE catheter for introduction into the area surrounding a cardiac valve to be treated. An ICE catheter (ICE=intracardiac echocardiography) should be understood to be a catheter with an ultrasonic transceiver system at its tip, which is able to create ultrasound images within the heart. The ICE catheter is further used to detect a relative position and/or a relative direction of orientation of the cardiac valve with respect to the ICE catheter with the aid of an ultrasound recording of the cardiac valve by the ICE catheter and preferably for ultrasound recordings of the prosthesis catheter. In addition, one part of the prosthetic cardiac valve implantation arrangement is a navigation system for determining an absolute position and an absolute direction of orientation of the ICE catheter. Hereinafter, an absolute position or absolute direction of orientation should be understood to mean a corresponding position or direction of orientation in a fixed coordinate system. This coordinate system can, for example, be a coordinate system in which the external navigation system is based and which is used by the external navigation system. On the other hand, relative positional data or directions of orientation should be understood as meaning corresponding information in a coordinate system, which moves or rotates together with moving components, in this case, the ICE catheter.

An absolute position and/or absolute direction of orientation of the cardiac valve is determined on the basis of the information relating to the relative position and/or the relative direction of orientation of the cardiac valve with respect to the ICE catheter and on the basis of the information relating to the absolute position and/or the absolute direction of orientation of the ICE catheter. If, for example, the positional data and/or orientation data are output as vectors, the absolute position of the cardiac valve with different coordinate systems of the ICE catheter and the navigation system can be determined by coordinate transformation and by simple vector addition of the transformed vectors relating to the relative position of the cardiac valve and the vectors relating to the absolute position of the ICE catheter. It is also possible for an absolute direction of orientation of the cardiac valve to be determined by vector addition of the relative direction of orientation of the cardiac valve with respect to the ICE catheter and the absolute direction of orientation of the ICE catheter.

The prosthetic cardiac valve implantation arrangement of an embodiment also comprises a control facility for controlling the insertion of the prosthetic cardiac valve into the annulus of the cardiac valve on the basis of the ultrasound recordings of the ICE catheter and positional and/or orientation-direction information in the navigation system.

Advantageously, the prosthetic cardiac valve implantation arrangement according to an embodiment of the invention achieves higher reliability and precision during the minimally invasive insertion of a prosthetic cardiac valve. The prosthetic cardiac valve implantation arrangement according to the invention enables the positioning of the prosthetic cardiac valve not only to be monitored and corrected, but, in the case of real-time processing of the position and orientation information, it is even also possible for the insertion of the prosthetic cardiac valve to be controlled properly so that no subsequent adjustment is now necessary. This enables the avoidance of complications, such as, for example, paravalvular leaks, so that the patient obtains optimum benefit from the prosthetic cardiac valve and it is possible to avoid after-treatment with an additional correcting element.

With the method for monitoring a catheter-based prosthetic cardiac valve implantation according to an embodiment of the invention, control commands are output by a control facility for the introduction of an ICE catheter into an area surrounding a cardiac valve to be treated. The control commands can, for example, be displayed to an attending physician on a screen display or it can also be alternatively or additionally used to control an automated system for the introduction of the ICE catheter in the vicinity of the cardiac valve to be treated.

A relative position and/or relative alignment or direction of orientation of the cardiac valve with respect to the ICE catheter is determined on the basis of ultrasound data on the cardiac valve recorded by the ICE catheter. In addition, an external navigation system is also used to determine an absolute position and/or absolute direction of orientation of the ICE catheter.

Furthermore, an absolute reference position and/or absolute reference direction of orientation of the cardiac valve is determined on the basis of the relative position of the cardiac valve determined and/or the relative direction of orientation of the cardiac valve determined and on the basis of the absolute position determined and/or the absolute direction of orientation of the ICE catheter determined.

In addition, for the implantation of a prosthetic cardiac valve, control commands are output for the introduction of a prosthesis catheter comprising a prosthetic cardiac valve as far as the absolute reference position of the cardiac valve determined.

Finally, control commands for the insertion of the prosthetic cardiac valve into the annulus of the cardiac valve are determined and output on the basis of received ultrasound data recorded by the ICE catheter and on the basis of positional and/or orientation-direction information from the navigation system. I.e., the ultrasound recordings from the ICE catheter are used, in combination with the information from the navigation system, for monitoring and controlling the positioning of the prosthesis catheter in the annulus of the cardiac valve.

The use according to an embodiment of the invention is directed at a use of a prosthetic cardiac valve implantation arrangement according to the invention to carry out an implantation of a prosthetic cardiac valve. Advantageously, the use of the prosthetic cardiac valve implantation arrangement according to the invention reduces the risk of an imprecisely positioned prosthetic cardiac valve so that the patient does not have to undergo a corrective intervention or suffer the negative consequences of an imprecisely positioned cardiac valve.

Some of the components of the prosthetic cardiac valve implantation arrangement according to an embodiment of the invention can be embodied substantially in the form of software components. This applies in particular to parts of the navigation system and the control facility. However, in principle, in particular when particularly fast calculations are required, these can also be partially implemented in the form of software-supported hardware, for example FPGAs or the like. Similarly, for example if only a transfer of data from other software components is involved, the required interfaces can be embodied as software interfaces. However, they can also be embodied as hardware-based interfaces controlled by suitable software.

A substantially software-based implementation has the advantage that, after supplementing the hardware by a navigation system and a corresponding modification of an ICE catheter, control facilities for prosthetic cardiac valve implantation arrangements used to date can also be easily retrofitted by a software update in order to work in accordance with an embodiment of the invention. Insofar, a corresponding non-transitory computer program product is disclosed with a computer program, which can be loaded directly into a storage facility of a control facility of a prosthetic cardiac valve implantation arrangement, with program sections for carrying all the steps of the method according to an embodiment of the invention when the program is executed in the control facility. In addition to the computer program, a non-transitory computer program product of this can optionally comprise additional components such as, for example, documentation and/or additional components including hardware components, such as, for example, hardware keys (dongles etc.) for using the software.

To transport the control facility and/or for storage on or in the control facility, it is possible to use a non-transitory computer-readable medium, for example a memory stick, a hard disk or another transportable or permanently installed data carrier on which the program sections of the computer program that can be read and executed by a computing unit of the control facility are stored. To this end, the computing unit can, for example, comprise one or more interacting microprocessors or the like.

The claims and the following description each contain particularly advantageous embodiments and developments of the invention. Here, in particular the claims of one claims category can also be developed analogously to the dependent claims of a category. In addition, within the context of the invention, the various features of different example embodiments and claims can also be combined to form new example embodiments.

In one particularly effective variant of the prosthetic cardiac valve implantation arrangement according to an embodiment of the invention, at least two position markers are arranged on the ICE catheter. The position markers are configured such that the position markers can be used by the navigation system to detect an absolute position and/or absolute direction of orientation of the ICE catheter.

The position markers can comprise inductors, such as, for example, current coils, which are excited by an electromagnetic field generated by an antenna of the navigation system to emit electromagnetic waves, which are in turn detected by a receiving antenna of the navigation system. The detected field strength or radiant power of the detected electromagnetic field can be used to draw conclusions regarding the distance between the position markers on the ICE catheter and the navigation system. The direction of the electromagnetic field emitted by the position markers can be used to determine a direction in which the position markers are located. Two such coils enable a determination of the direction or a determination of the relative positions of the two position markers with respect to one another thus enabling the determination of a direction of orientation of the ICE catheter tip.

In an alternative variant of the prosthetic cardiac valve implantation arrangement according to an embodiment of the invention, the at least two position markers are arranged on a tip of the ICE catheter with an ultrasound source thus enabling a position and/or direction of orientation of the ultrasound source of the ICE catheter to be determined. In the case of an ICE catheter, there is usually an ultrasound source on the tip of the catheter so that an arrangement of the position markers on the tip of the catheter enables the determination of the position and/or direction of the ultrasound source. Since the ultrasound source is used to record ultrasound images, the determination of the position and orientation of the catheter tip can be used to draw conclusions regarding a position from which the ultrasound images were recorded. This also enables conclusions to be drawn regarding the viewing angle for the recording of the ultrasound images. If the ultrasound image generates a three-dimensional image, for example a slice image from a plurality of two-dimensional images, the absolute position of individual image points of the three-dimensional image can determined on the basis of the knowledge of the position and orientation of the catheter tip.

In one particularly effective embodiment of the prosthetic cardiac valve implantation arrangement according to the invention, the ICE catheter is configured to create 2D ultrasound images in several planes and/or 3D ultrasound images of the cardiac valve for the determination of an absolute reference position and/or absolute reference direction of orientation of the cardiac valve. As mentioned above, absolute positions can be assigned to individual image points on the basis of the ultrasound images. This in particular enables the determination of an absolute reference position and/or absolute reference direction of orientation of the cardiac valve which can be used later as comparative values when checking whether an inserted prosthetic cardiac valve has been inserted correctly.

In one variant of the prosthetic cardiac valve implantation arrangement according to an embodiment of the invention, the control facility is configured to determine an absolute reference position of the cardiac valve by moving the ICE catheter to the position of the cardiac valve and determining the absolute position of the ICE catheter at this position with the aid of the navigation system. With this variant, it is, for example, possible for the ICE catheter, which is, for example, initially located in the apical region of the left ventricle, to be introduced as far as the cardiac valve. The location of the cardiac valve or the base of the valve, also called the annulus, can also be determined in this way, wherein in this case the ultrasound images not do not have to be laboriously analyzed since the images only have to be used to determine that the ICE catheter or the ultrasound sensor thereof is located directly at the location of the cardiac valve or the annulus. Subsequently, the ICE catheter is returned to the apical region of the heart and its position. From there, during the procedure of the insertion of the prosthetic cardiac valve with the aid of a prosthesis catheter, it is then possible to record further ultrasound images, which are used for the control or monitoring of the implantation process.

In another variant of the prosthetic cardiac valve implantation arrangement according to an embodiment of the invention, the prosthetic cardiac valve implantation arrangement comprises a display for the simultaneous depiction of information relating to the position and/or orientation of the prosthetic cardiac valve and the ultrasound images for monitoring the insertion of the prosthetic cardiac valve into the annulus of the cardiac valve. The display can, for example, be part of the navigation system or an ultrasound device connected to the ICE catheter. Alternatively, the display can also be arranged in a separate unit. Advantageously, the display of the image provides the user with information as to where exactly the prosthetic cardiac valve catheter is located when introduced. Furthermore, the display can also be used for the depiction and monitoring of the insertion of the prosthetic cardiac valve in the region of the cardiac valve. For example, the user can compare the positional data with the previously recorded reference data for the position and orientation of the cardiac valve and hence determine whether the prosthetic cardiac valve is already positioned and aligned correctly. Alternatively, the checking with respect to correct positioning and alignment of the prosthetic cardiac valve can also be substantially automated, wherein the measured values acquired are continuously compared with the reference values and, in the event of a threshold value for a deviation of these vales being fallen below, correct positioning and alignment of the prosthetic cardiac valve is notified.

It is particularly preferable for the insertion of the prosthetic cardiac valve into the annulus of the cardiac valve, for the control facility to be configured to determine and monitor an absolute position and/or absolute direction of orientation of the prosthesis catheter from a new ultrasound recording with the aid of the ICE catheter in conjunction with positional and/or orientation data from the navigation system. This enables the position and orientation of the prosthetic cardiac valve to be monitored, preferably continuously, as early as the introduction of the prosthetic cardiac valve toward the basis of the cardiac valve so that the prosthetic cardiac valve can be maneuvered to the correct position quasi by remote control without any subsequent corrections having to be made.

In one variant of the prosthetic cardiac valve implantation arrangement according to an embodiment of the invention, the control facility is configured to check the correct insertion of the prosthetic cardiac valve on the basis of a comparison of the current position and/or current direction of orientation of the prosthetic cardiac valve with the absolute reference position determined and/or absolute reference direction of orientation of the cardiac valve. In the comparison with the reference values, if a predetermined threshold value for the maximum deviation to be tolerated is fallen below, this can be used as a criterion with respect to correct positioning and alignment of the prosthetic cardiac valve.

In one embodiment of the prosthetic cardiac valve implantation arrangement according to the invention, the prosthetic cardiac valve implantation arrangement comprises a signal output unit, which is configured, in the event that a correct position of the prosthetic cardiac valve was determined, to output an optical and/or audible signal. For example, as a sign of the attainment of a correct position of the prosthetic cardiac valve, a "traffic light" in the user's field of view is switched from the color "red" to "green". The audible signal is able, similarly to the signal on a parking aid, for example, to indicate an approximation of the correct position of the prosthetic cardiac valve by increasing the frequency of a signal sequence in dependence upon an approximation of the correct position. When the correct position is achieved, it is possible for a lengthy persistent tone to be output.

In one variant of the prosthetic cardiac valve implantation arrangement according to an embodiment of the invention, the prosthetic cardiac valve implantation arrangement can comprise a segmentation unit, which is configured to use an ultrasound image recording of the prosthetic cardiac valve to perform a segmentation of the prosthetic cardiac valve and to mark the segmented prosthetic cardiac valve in a displayed image. For example, for the segmentation, the prosthetic cardiac valve is initially depicted with the aid of the ICE catheter and then the prosthetic cardiac valve is marked on the depiction by segmentation so that the position and orientation of the inserted prostheses are clear to the user. The segmentation can, for example, take place in that the position of the cardiac valve is known by the navigation system and this position is used as a seed point for automated segmentation. Alternatively, the cardiac valve, or the base of the valve, displayed on the ultrasound images can also be provided manually with, for example, an image marking, also known as a region of interest (ROI).

In a particularly user-friendly variant of the prosthetic cardiac valve implantation arrangement according to an embodiment of the invention, the signal output unit is configured, in the event of a deviation from a correct position and/or a correct orientation of the prosthetic cardiac valve, to display the deviation from a correct position and/or orientation of the prosthetic cardiac valve optically or acoustically. This enables the user to correct the positioning of the prosthetic cardiac valve selectively with reference to the display thus saving effort and time and therefore increasing the patient's comfort and safety. The deviation in position can, for example, be identified by different colors in dependence upon the degree of the deviation. Alternatively or additionally, the deviation in orientation can be indicated by tones, wherein a continuous tone means that the level of the base of the valve has been reached correctly. Tone sequences with different pauses between the tones or different frequencies can indicate the distance from the correct position, as with a parking aid.

In one embodiment of the use according to the invention, the cardiac valve is an aortic valve. Alternatively, the cardiac valve can be a mitral valve, a tricuspid valve or a pulmonary valve. The function of the aortic valve is to prevent backflow of the blood into the left ventricle in order to achieve optimum pumping action. Correct function of the aortic valve is vital since, on a dysfunction, there is a gradual overloading of the left ventricle accompanied by a reduction in the contractility of the left ventricle resulting in a reduction in the patient's physical capacity and ultimately also the patient's life expectancy. Therefore, it is advisable to replace a defective aortic valve at the correct time in order to prevent or stop the described impairment of the condition of the cardiac muscle.

Figure 1:
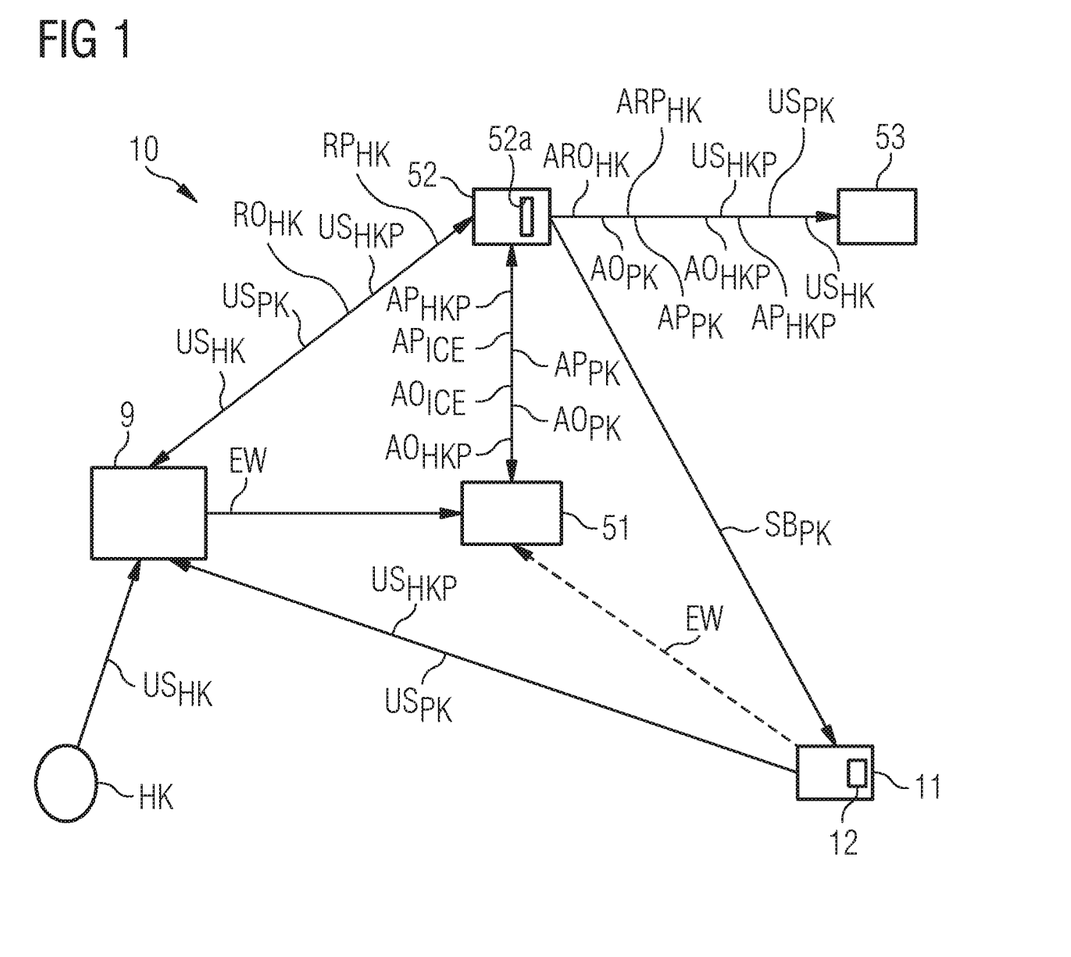
FIG. 1 a schematic view of a prosthetic cardiac valve implantation arrangement according to an example embodiment of the invention, FIG. 2 a sectional view of a heart with a still unfolded TAVI catheter, FIG. 3 a sectional view of a heart with an unfolded TAVI catheter and an ICE catheter in the right atrium of the heart, FIG. 4 sectional view of a heart with an unfolded TAVI catheter and an ICE catheter in the left ventricle of the heart, FIG. 5 a flow diagram illustrating a method for monitoring a catheter-based prosthetic cardiac valve implantation according to an example embodiment of the invention.

In FIG. 1 is a schematic view of a prosthetic cardiac valve implantation arrangement 10 according to an example embodiment of the invention. The prosthetic cardiac valve implantation arrangement 10 comprises a navigation system 51 arranged, for example, outside a patient's body. The prosthetic cardiac valve implantation arrangement 10 also comprises an ICE catheter 9 to be inserted into a ventricle assigned to a cardiac valve HK to be treated. The ICE catheter 9 is moreover configured to record ultrasound images $US_{HK}$ from the interior of the heart, in particular a cardiac valve HK to be treated. With the aid of an evaluation unit 52a, which in the example embodiment shown in FIG. 1 is part of a control facility 52, which is also part of the prosthetic cardiac valve implantation arrangement 10, the ultrasound images $US_{HK}$ can be used as the basis for determining a relative position $RP_{HK}$ and a relative alignment $RO_{HK}$ of the cardiac valve HK with respect to the ICE catheter 9 (see FIG. 5, Step 5.III).

The navigation system 51 is used to determine an absolute position $AP_{ICE}$ and absolute direction of orientation $AO_{ICE}$ of the ICE catheter 9. To this end, the ICE catheter 9 comprises a plurality of position markers (not shown) at its tip. These position markers comprise current coils (not shown), which are excited by an electromagnetic field generated by an antenna of the navigation system 51 to emit electromagnetic waves EW, which are in turn detected by a receiving antenna of the navigation system 51. The detected field strength or radiant power of the detected electromagnetic field can be used to draw conclusions regarding the distance between the position markers of the ICE catheter 9 and the navigation system 51. The direction of the electromagnetic field emitted by the position markers can be used to determine a direction in which the position markers are located. Two such coils permit a determination of the direction or determination of the relative positions of the two position markers with respect to one another thus enabling the determination of a direction of orientation of the ICE catheter tip with the aid of the navigation system 51.

On the basis of the data relating to the absolute position $AP_{ICE}$ and absolute direction of orientation $AO_{ICE}$ of the ICE catheter 9 and on the basis of the ultrasound images $US_{HK}$ of the cardiac valve HK recorded by the ICE catheter 9, the evaluation facility 52a determines an absolute reference position $ARP_{HK}$ and absolute reference direction of orientation $ARO_{HK}$ of the cardiac valve HK and these are, for example, output on a display unit 53. The display unit 53 can also provide a graphical depiction of the ultrasound images $US_{HK}$ recorded by the ICE catheter 9.

A further part of the prosthetic cardiac valve implantation arrangement 10 is a prosthesis catheter 11, which, during the implantation of a prosthetic cardiac valve, is initially introduced as far as the absolute reference position $ARP_{HK}$ of the cardiac valve HK determined. The introduction of the prosthesis catheter 11 can also be controlled by automated means via control commands $SB_{PK}$ from the control facility 52 taking account of the absolute reference position $ARP_{HK}$ determined.

For the insertion of the prosthetic cardiac valve 12 of the prosthesis catheter 11, the control facility 52 issues control commands to the ICE catheter 9 to record ultrasound images $US_{PK}$ of the prosthesis catheter 11, which, after introduction, is located in the vicinity of the position of the cardiac valve HK. The ultrasound image recordings $US_{PK}$ from the prosthesis catheter 11 are sent to the control facility 52, which, on the basis of these ultrasound image recordings $US_{PK}$, determines a relative position $RP_{PK}$ of the prosthesis catheter 11 with respect to the ICE catheter 9. On the basis of the known absolute position $AP_{ICE}$ of the ICE catheter 9 and the relative position $RP_{PK}$ of the prosthesis catheter 11 with respect to the ICE catheter 9, the evaluation facility 52a determines an absolute position $AP_{PK}$ of the prosthesis catheter 11.

Analogously, the evaluation unit 52a can also determine an absolute direction of orientation $AO_{PK}$ of the prosthesis catheter 11. On the basis of the values $AP_{PK}$, $AO_{PK}$ determined for the position and orientation of the prosthesis catheter and on the basis of the absolute reference position $ARP_{HK}$ determined and the absolute reference direction of orientation $ARO_{HK}$ of the cardiac valve HK, the evaluation unit 52a determines a change to the position and change to the orientation of the prosthesis catheter 11 in order to arrive at the absolute reference position $ARP_{HK}$ determined and the absolute reference direction of orientation $ARO_{HK}$ determined. To this end, the control facility 52 issues corresponding control commands $SB_{PK}$ with which the prosthesis catheter 11 is moved to the desired position and in the desired direction of orientation.

Figure 3:
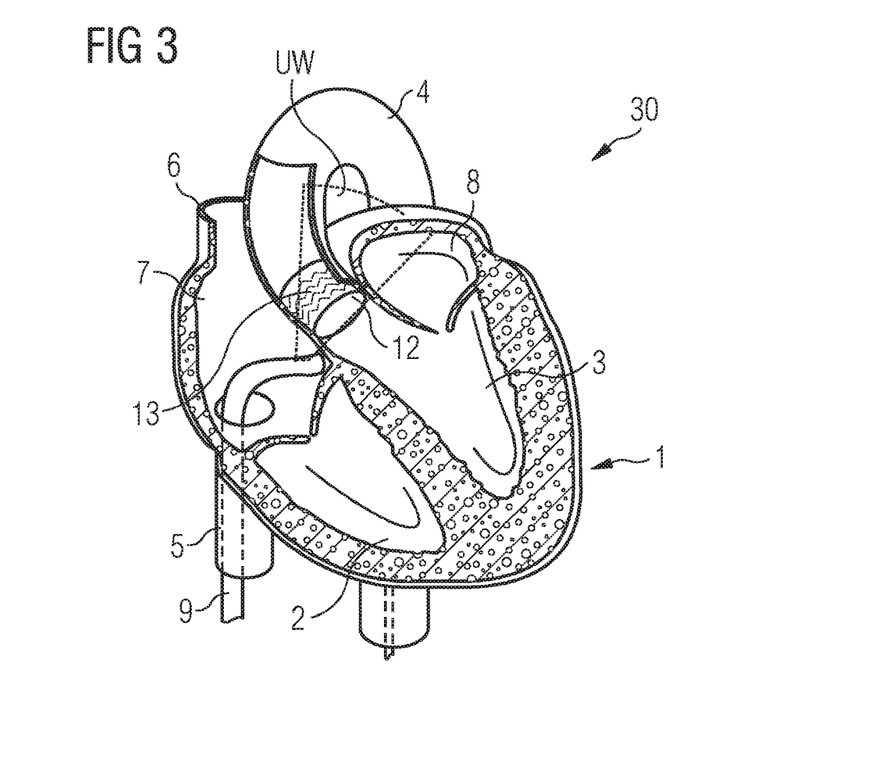

When it has arrived at the position in the annulus of the cardiac valve HK, the prosthetic cardiac valve 12 of the cardiac valve catheter 11 is unfolded (see FIG. 3). Then, an ultrasound image $US_{HKP}$ of the prosthetic cardiac valve 12 is recorded by ICE catheter 9 and in turn sent to the control facility 52. The evaluation facility 52a of the control facility 52 now determines on the basis of the knowledge of the correct absolute position $ARP_{HK}$ and correct absolute orientation $ARO_{HK}$ of the cardiac valve HK, possibly with the assistance of the user, who is shown the ultrasound image $US_{HKP}$ of the prosthetic cardiac valve 12 on the display 53, whether the prosthetic cardiac valve 12 is located at the correct position in the correct orientation. If this is the case, the user is given a signal indicating that the implantation has taken place successfully. Otherwise, the user is informed that it is necessary to correct the position and/or orientation of the prosthetic cardiac valve 12. Further corrections can be made in the way described both by the user, possibly in a semi-automated manner, by inputting commands to the control facility 52 or even in an automated manner by the determination of a correction process by the control facility 52 itself.

Alternatively or additionally, the prosthesis catheter 11 and/or prosthetic cardiac valve 12 can also comprise position markers, which function analogously to the position markers of the ICE catheter 9. This enables the position and orientation of the prosthesis catheter 11 and/or prosthetic cardiac valve 12 during the insertion process to be determined directly with the aid of the navigation system 51. The positional data $AP_{PK}$, $AO_{PK}$, $AP_{HKP}$, $AO_{HKP}$ on the prosthesis catheter 11 and the prosthetic cardiac valve 12 determined by the navigation system is sent to the control facility 52 where it is used in the evaluation unit 52a, with the involvement of the reference values $ARO_{HK}$, $ARP_{HK}$ as mentioned several times above, to check correct positioning or alignment of the prosthesis catheter 11 or the prosthetic cardiac valve 12. It is also possible for said data $AP_{PK}$, $AO_{PK}$, $AP_{HKP}$, $AO_{HKP}$ to be depicted pictorially on the display 53.

Figure 2:
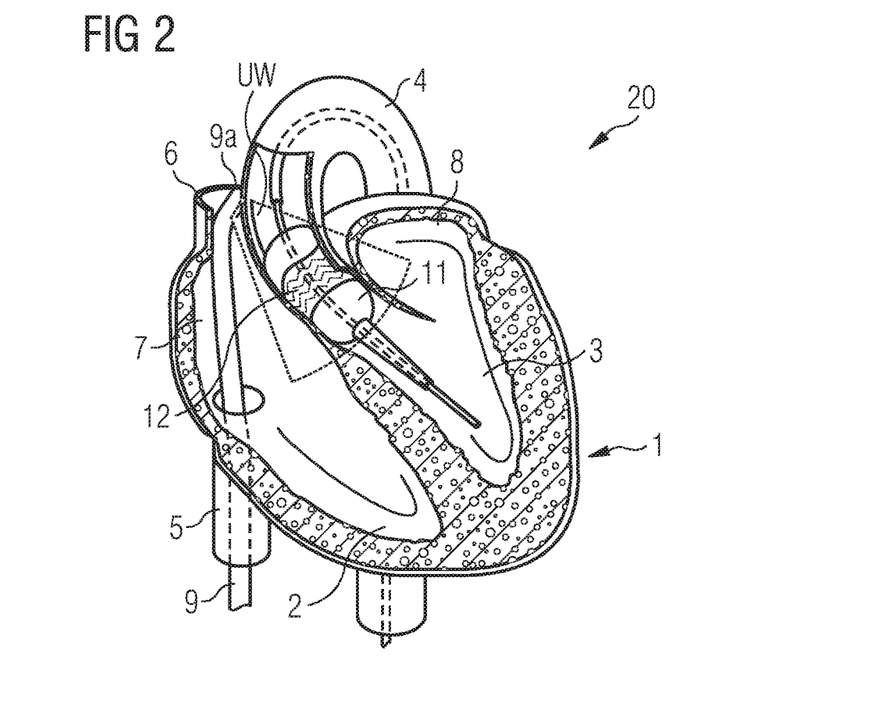

FIG. 2 is a sectional view 20 of a heart 1 with a still unfolded prosthesis catheter 11. The heart 1 comprises a right ventricle 2, a left ventricle 3, a right atrium 7 and a left atrium 8. An inferior vena cava 5 and a superior vena cava 6 empty into the right atrium 7. The aorta 4 empties into the left ventricle 3. The prosthesis catheter 11 is pushed through the aorta 4 as far as a position of the aortic valve. The prosthesis catheter 11 comprises a prosthetic cardiac valve 12, which, in the condition shown in FIG. 2, is still stowed in the catheter 11 and has not yet been unfolded. The prosthesis catheter 11 is already located at the position of the aortic valve. FIG. 2 also shows an ICE catheter 9 that has been pushed through the inferior vena cava 5 into the right atrium 2 from where it records an ultrasound image of the prosthesis catheter 11. FIG. 2 shows ultrasound waves UW emitted by the tip 9a of the ICE catheter 9 in the direction of the prosthesis catheter 11 and with which an image of the prosthesis catheter 11 and the environment thereof is generated. Comparison with a previously determined reference position and reference orientation of the cardiac valve now enables it to be determined whether the catheter 11 is located at the correct position and is also correctly oriented.

FIG. 3 also shows a sectional view 30 of a heart 1, but now with a biological prosthetic cardiac valve 12 that has already been inserted. Like the heart 1 depicted in FIG. 2, the heart depicted in FIG. 3 comprises a right ventricle 2, a left ventricle 3, a right atrium 7, a left atrium 8, an inferior vena cava 5, a superior vena cava 6 and an aorta 4. The biological prosthetic cardiac valve 12 is now seated at the location of the aortic valve. It comprises a type of grid construction 13, which has been pressed with the aid of the prosthesis catheter 11 (see FIG. 2) against the internal wall of the aorta in the region of the aortic valve. In the stage shown in FIG. 3, the prosthesis catheter 11 itself has already been removed from the region of the aortic valve. The position and alignment of the prosthetic cardiac valve 12 can now be monitored with the aid of the ICE catheter 9 and a navigation system 51 (see FIG. 1) in that the ICE catheter 9 is used to record ultrasound images of the prosthetic aortic valve 12 and, from these images in combination with the navigation data from the navigation system 51 (see FIG. 1), values are determined with respect to the current position and alignment of the prosthetic aortic valve 12. These measured values are then compared with reference values relating to an absolute cardiac valve position and an absolute cardiac valve orientation direction. If the comparison determines excessive deviation, it is, for example, possible to correct the position and alignment of the prosthetic aortic valve 12 with the aid of the prosthesis catheter 11 (see FIG. 2).

Figure 4:
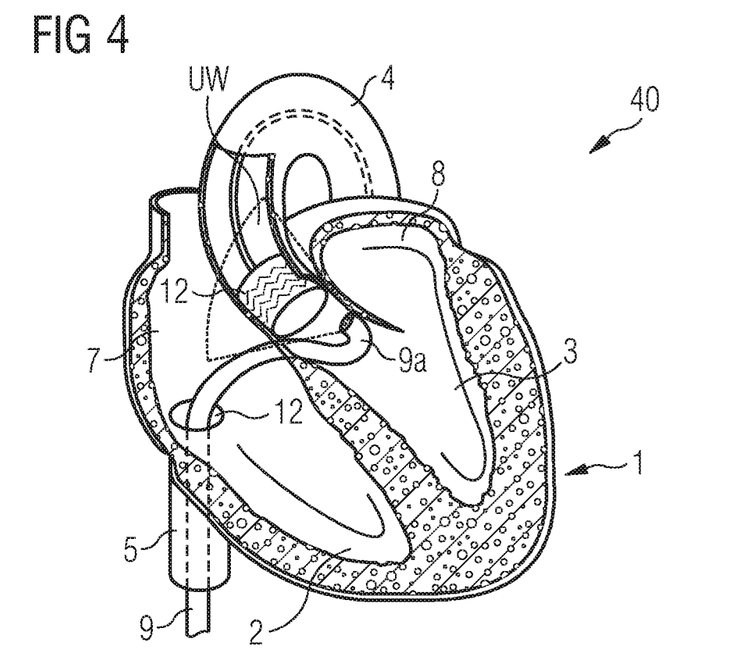

FIG. 4 is sectional view 40 of a heart 1 with a prosthetic aortic valve 12 and an ICE catheter 9 in the left ventricle 3 of the heart 1. Like the heart 1 depicted in FIG. 2 and FIG. 3, the heart depicted in FIG. 4 comprises a right ventricle 2, a left ventricle 3, a right atrium 7, a left atrium 8, an inferior vena cava 5, a superior vena cava 6 and an aorta 4. In this case, the ICE catheter 9 or the tip thereof 9a is therefore positioned differently from the example embodiments shown in FIG. 2 and FIG. 3 for monitoring the position and alignment of the prosthetic aortic valve 12 in the left ventricle 3. From there, ultrasound images of the prosthetic aortic valve 12 are again recorded with the aid of the ICE catheter 9. Then, analogously to the procedure mentioned in conjunction with FIG. 3, the current position and alignment of the prosthetic aortic valve 12 is determined on the basis of these images in combination with the navigation data from the navigation system. These measured values are then compared with reference values. If the comparison determines excessive deviation, it is, for example, possible for the position and alignment of the prosthetic aortic valve 12 to be corrected.

Figure 5:
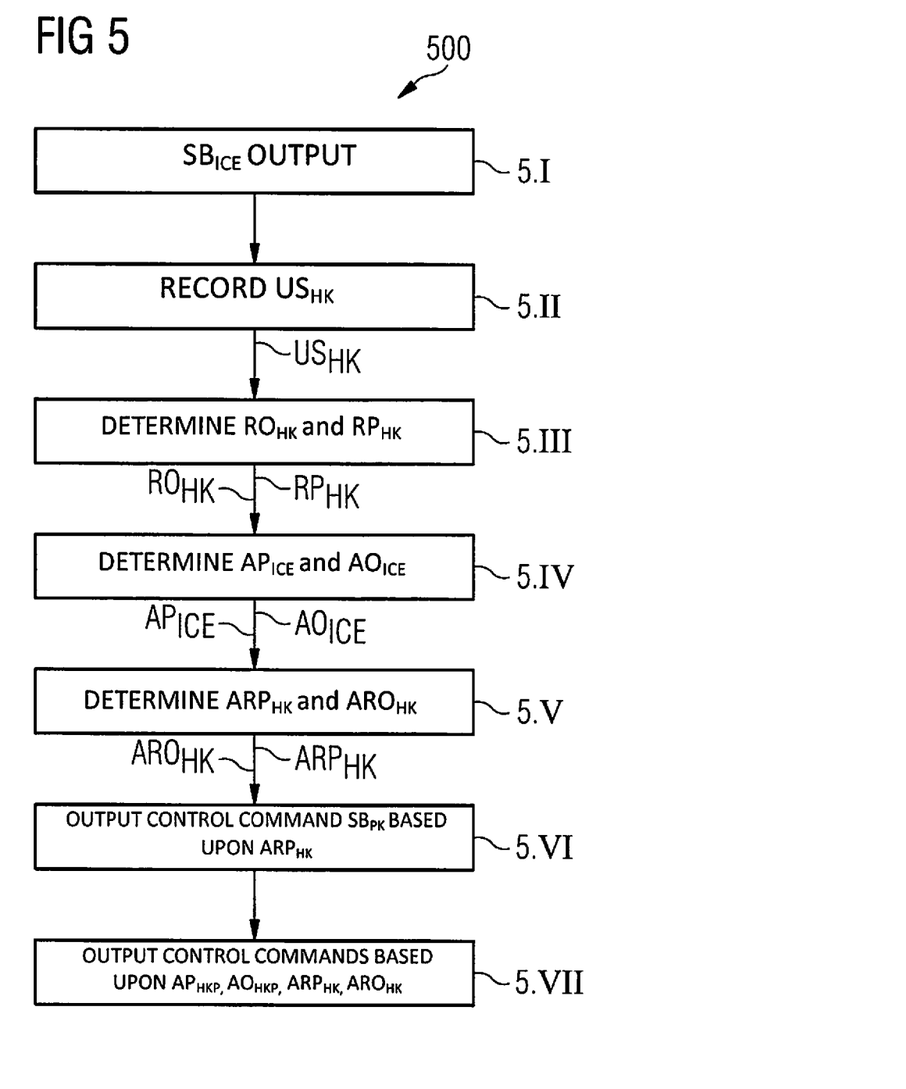

FIG. 5 is a flow diagram 500 illustrating a method for monitoring a catheter-based prosthetic aortic valve implantation according to an example embodiment of the invention. With this method, an ICE catheter is used in conjunction with a navigation system and, during a TAVI procedure, together they determine information relating to the position $AP_{HKP}$ and the alignment $AO_{HKP}$ of a prosthetic aortic valve. In this case, it is in particular determined whether the prosthetic aortic valve is located at the correct position and aligned in a planar manner in the old base of the valve and has been correctly expanded or inserted.

Within the framework of the method, initially in a Step 5.I, a control command $SB_{ICE}$ for the introduction of an ICE catheter 9 via the inferior vena cava into the atrium of the right ventricle 2 is output via a control facility 52 (see FIG. 1) (see FIG. 2). It is also optionally possible for a control command $SB_{ICE}$ to be issued for the introduction of the ICE catheter 9 into the left ventricle 3 via a passage between the right atrium 7 and the left ventricle 3 by puncturing (see FIG. 4).

During the continuation of the method, a navigation system 51 (see FIG. 1) arranged outside the body of the patient monitors an absolute position $AP_{ICE}$ of the ICE catheter 9 and the alignment thereof. $AO_{ICE}$. To this end, the ICE catheter 9 comprises at its tip a plurality of position markers, which, for example, each comprise a coil and, following an induction process by the electromagnetic waves emitted by the navigation system 51, are used to emit electromagnetic waves such that they can be received by a receiving antenna of the navigation system 51. For example, a distance between the receiving antenna of the navigation system 51 and the respective position markers can be determined from the detected field strength or radiant power. The use of at least two position markers enables the orientation of the tip 9a of the ICE catheter 9 to be determined.

In a Step 5.II, ultrasound images $US_{HK}$ of the aortic valve in the heart of the patient are recorded with the aid of the ICE catheter 9 (see FIG. 1, 2, 3, 4). These can, for example, be two-dimensional images in several planes or three-dimensional images. In the Step 5.III, the images $US_{HK}$ are used to determine a relative position $RP_{HK}$ and relative alignment or orientation $RO_{HK}$ of the aortic valve relative to the ICE catheter tip 9a (see FIG. 2). Furthermore, in a Step 5.IV, an absolute position $AP_{ICE}$ and absolute direction of orientation $AO_{ICE}$ of the ICE catheter 9 or the tip 9a of the ICE catheter 9 are determined with the aid of the navigation system 51.

Then, in a Step 5.V, an absolute reference position $ARP_{HK}$ of the cardiac valve and the absolute reference orientation $ARO_{HK}$ thereof is determined on the basis of the relative position $RP_{HK}$ determined or relative orientation $RO_{HK}$ and the absolute position $AP_{ICE}$ and absolute orientation $AO_{ICE}$ of the ICE catheter tip 9a monitored by the navigation system 51.

Then, in a Step 5.VI, a control command $SB_{PK}$ is output to initiate a transfer of a prosthesis catheter 11 within the framework of a TAVI procedure via the aorta as far as the absolute reference position $ARP_{HK}$ of the aortic cardiac valve determined. Finally, in a Step 1.VII, control commands are output to control the insertion of the prosthetic aortic cardiac valve 12 into the annulus of the aortic cardiac valve on the basis of ultrasound image recordings $US_{HKP}$ of the ICE catheter 9 and positional and/or orientation-direction information $AP_{HKP}$, $AO_{HKP}$ from the navigation system 51 and on the basis of the known reference position $ARP_{HK}$ and known reference orientation $ARO_{HK}$ of the cardiac valve.

Finally, reference is made once again to the fact that the above-described method and device are only preferred example embodiments of the invention and the invention can be varied by the person skilled in the art without departing from the scope of the invention as specified in the claims. The invention is not restricted to use on the aortic valve but can also, in principle, be applied to the insertion of prosthetic cardiac valves for the pulmonary valve, the tricuspid valve or the mitral valve. For purposes of completeness, reference is also made to the fact that the use of the indefinite article "a" or "an" does not preclude the possibility that the features in question may also be present on a multiple basis. Similarly, the term "unit" does not preclude the possibility of the unit comprising a plurality of components, which could also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A prosthetic cardiac valve implantation arrangement, comprising: a prosthesis catheter, including a prosthetic cardiac valve to be inserted; an ICE catheter for introduction into an area surrounding a cardiac valve to be treated, and to detect at least one of a relative position and relative direction of orientation of the cardiac valve with respect to the ICE catheter with aid of at least one ultrasound image of the cardiac valve recorded by the ICE catheter; a navigation system to determine an absolute position and absolute direction of orientation of the ICE catheter; and a control facility to control insertion of the prosthetic cardiac valve into an annulus of the cardiac valve based upon ultrasound images recorded by the ICE catheter and at least one of the absolute position and absolute direction of orientation determined by the navigation system, wherein the ICE catheter is configured to create at least one of 2D ultrasound images in several planes and 3D ultrasound images of the cardiac valve to determine at least one of an absolute reference position and an absolute reference direction of orientation of the cardiac valve, a display to simultaneously depict information with respect to at least one of an absolute position and an absolute orientation of the prosthetic cardiac valve and the at least one of 2D and 3D ultrasound images for monitoring the insertion of the prosthetic cardiac valve into the annulus of the cardiac valve, and wherein the control facility is further configured to check correct insertion of the prosthetic cardiac valve based upon a comparison of at least one of a current position and a current direction of orientation of the prosthetic cardiac valve with a respective at least one of the absolute reference position determined and the absolute reference direction of orientation of the cardiac valve determined.

2. The prosthetic cardiac valve implantation arrangement of claim 1, wherein at least two position markers, configured such that the at least two position markers are usable by the navigation system to detect at least one of the absolute position and the absolute direction of orientation of the ICE catheter, are arranged on the ICE catheter.

3. The prosthetic cardiac valve implantation arrangement of claim 2, wherein the at least two position markers are arranged on a tip of the ICE catheter with an ultrasound source so that at least one of a position and direction of orientation of the ultrasound source of the ICE catheter are acquirable by the detection of the at least one of the position and direction by the navigation system using the position markers.

4. The prosthetic cardiac valve implantation arrangement of claim 1, wherein the control facility is configured to determine an absolute reference position of the cardiac valve by moving the ICE catheter to a position of the cardiac valve and by determining the absolute position of the ICE catheter at the position of the cardiac valve using the navigation system.

5. The prosthetic cardiac valve implantation arrangement of claim 1, wherein the control facility is configured, for the insertion of the prosthetic cardiac valve into the annulus of the cardiac valve, to determine and monitor at least one of the absolute position and the absolute direction of orientation of the prosthesis catheter by recording a new ultrasound image using the ICE catheter in conjunction with at least one of positional and orientation data from the navigation system.

6. The prosthetic cardiac valve implantation arrangement of claim 1, further comprising at least one of
  a signal output unit, configured, upon a correct position of the prosthetic cardiac valve being determined to output at least one of an optical and audible signal; and
  a segmentation unit, configured to use an ultrasound image of the prosthetic cardiac valve to perform a segmentation of the prosthetic cardiac valve to create a segmented prosthetic cardiac valve, and to mark the segmented prosthetic cardiac valve in a displayed image.

7. The prosthetic cardiac valve implantation arrangement of claim 6, wherein prosthetic cardiac valve implantation arrangement includes at least the signal output unit and wherein the signal output unit is configured, upon occurrence of a deviation from at least one of the correct position determined and a correct orientation of the prosthetic cardiac valve, to at least one of optically and acoustically display the deviation from the at least one of the correct position and the correct orientation of the prosthetic cardiac valve.

8. The prosthetic cardiac valve implantation arrangement of claim 1, wherein the ICE catheter is further configured to record ultrasound images of the prosthesis catheter.

9. A method, comprising:
using the prosthetic cardiac valve implantation arrangement of claim 1 to carry out implantation of the prosthetic cardiac valve.

10. The method claim 9, wherein the cardiac valve is an aortic valve.

\* \* \* \* \*